(12) United States Patent
Vennemann et al.

(10) Patent No.: US 8,044,065 B2
(45) Date of Patent: Oct. 25, 2011

(54) BENZOTHIENOPYRIDINES FOR USE AS INHIBITORS OF EG5 KINESIN

(75) Inventors: Matthias Vennemann, Constance (DE); Thomas Baer, Reichenau (DE); Gudrun Groegor, Reichenau (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 12/749,623

(22) Filed: Mar. 30, 2010

(65) Prior Publication Data

US 2010/0183550 A1 Jul. 22, 2010

Related U.S. Application Data

(62) Division of application No. 11/659,738, filed on Mar. 6, 2007, now Pat. No. 7,718,665.

(30) Foreign Application Priority Data

Aug. 18, 2004 (EP) .................................... 04103958
Aug. 31, 2004 (EP) .................................... 04104175

(51) Int. Cl.
*A61K 31/437* (2006.01)
(52) U.S. Cl. ...................................................... 514/287
(58) Field of Classification Search .................... 514/287
See application file for complete search history.

(56) References Cited

U.S. PATENT DOCUMENTS

| 6,890,933 B1 | 5/2005 | Feng et al. |
|---|---|---|
| 2003/0113822 A1 | 6/2003 | Westwood et al. |
| 2003/0114432 A1 | 6/2003 | Clare et al. |
| 2004/0242596 A1 | 12/2004 | Kim |
| 2005/0004156 A1 | 1/2005 | Feng et al. |
| 2007/0232596 A1 | 10/2007 | Vennemann et al. |

FOREIGN PATENT DOCUMENTS

| EP | 0 357 122 | 3/1990 |
|---|---|---|
| WO | WO 96/32003 | 10/1996 |
| WO | WO 02/28865 | 4/2002 |
| WO | WO 2004/004652 | 1/2004 |
| WO | WO 2004/111193 | 12/2004 |
| WO | PCT/EP2005/054054 | 11/2005 |
| WO | WO 2006/086358 | 8/2006 |
| WO | PCT/EP2007/051688 | 5/2007 |
| WO | PCT/EP2007/051691 | 5/2007 |
| WO | PCT/EP2007/055846 | 6/2007 |
| WO | WO 2007/144384 | 12/2007 |
| WO | PCT/EP2007/057195 | 1/2008 |
| WO | WO 2008006883 | 1/2008 |

OTHER PUBLICATIONS

Hammam, A., et al. "Synthesis of Novel Tricyclic Heterocyclic Compounds as Potential Anticancer Agents Using Chromanone and Thiochromanone as Synthons." (Indian Journal of Chemistry), 2003, 1985-1993, 42B.

Toth, G., et al. "Fused Heterocycles. Part 3. Synthesis and Stereochemistry of Benzopyrano-and Benzothiapyrano-[4, 3-c] Pyrazoles." (Journal of the Chemical Society), 1989, 319-323, 2.

"GI50 Mean Graph for Compound 652810-NCI Cancer Screen Aug. 2004 Data." (DTP Warehouse), 2004, 1, XP002420061.

Sunder-Plassmann, N., et al. "Synthesis and biological evaluation of new tetrahydro-Beta-carbolines as inhibitors of the mitotic kinesin Eg5," Bioorganic & Medicinal Chemistry, vol. 13, pp. 6094-6111 (2005).

Blicke and D. Sheets, "Derivatives of Thianaphthene," *J. Am. Chem, Soc.*, v. 70, pp. 3768-3770, 1948.

Marcus et al., "Mitotic Kinesin Inhibitors Induce Mitotic Arrest and Cell Death in Taxol-resistant and -sensitive Cancer Cells." *J. Biol. Chem.*, v.280:12, pp. 11569-11577, 2005.

Hotha et al., "HR22C16: A Potent Small-Molecule Probe for the Dynamics of Cell Division." *Angew. Chem.*, v.115, pp. 2481-2484, 2003.

Avakian et al., "The Synthesis and Microbiological Properties of β-(2-Benzothienyl)-α-aminopropionic Acid." *J. Am. Chem. Soc.*, v.70, pp. 3075-3076, 1948.

Roschke Anna V., et al., "Karyotypic Complexity of the NCI-60 Drug-Screening Panel", Cancer Research 63, 8634-8647, Dec. 15, 2003.

*Primary Examiner* — Bruck Kifle
(74) *Attorney, Agent, or Firm* — Millen, White, Zelano & Branigan, P.C.

(57) ABSTRACT

Compounds of a certain formula I, in which R1, R2, R3, R4 and X have the meanings indicated in the description, are novel effective compounds with Eg5 inhibitory, anti-proliferative and/or apoptosis inducing activity.

14 Claims, No Drawings

BENZOTHIENOPYRIDINES FOR USE AS INHIBITORS OF EG5 KINESIN

This application is a divisional application of U.S. patent application Ser. No. 11/659,738 filed Mar. 6, 2007 now U.S. Pat. No. 7,718,665.

FIELD OF APPLICATION OF THE INVENTION

The invention relates to novel classes of indolopyridine, benzofuranopyridine and benzothienopyridine derivatives, which can be used in the pharmaceutical Industry for the production of pharmaceutical compositions.

PRIOR ART

In the document Hotha et al., Angew. Chem. 2003, 115, 2481-2484 the indolopyridine compound HR22C16 is described as inhibitor of cell division by targeting Eg5.

EP357122 contains, inter alia, indolopyridine, benzofuranopyridine and benzothienopyridine derivatives as cytostatic compounds.

In the International Applications WO9632003 and WO0228865 indolopyridine derivatives are described with PDE inhibitory activity.

In the International Application WO 2004/004652, inter alia, trans-10-(3-hydroxy-phenyl)-2-methyl -3a,4,9,10-tetrahydro-2,9,10a-triaza-cyclopenta[b]fluorene-1,3-dione is described in a crystallized complex with the kinesin spindle protein (KSP).

In the US-application US 2005/0004156 indolopyridine derivatives, specifically monastroline derivatives, are described as Eg5 inhibitors.

DESCRIPTION OF THE INVENTION

It has now been found that the novel indolopyridine, benzofuranopyridine and benzothienopyridine derivatives, which are described in greater details below, differ from prior art compounds by unanticipated structural features and have surprising and particularly advantageous properties. Thus, for example, the compounds according to this invention can act as inhibitors of Eg5 kinesin. In more detail, it has been unexpectedly found that these derivatives are potent and highly efficacious inhibitors of cellular (hyper)proliferation and/or cell-cycle specific inducers of apoptosis in cancer cells. Therefore, unanticipatedly, these compounds can be useful for treating hyperproliferative diseases and/or disorders responsive to the induction of apoptosis, in particular cancer. By having a cell-cycle specific mode of action, these derivates should have a higher therapeutic index compared to standard chemotherapeutic drugs targeting basic cellular processes like DNA replication or interfering with basic cellular molecules like DNA.

Thus, for example, the compounds according to this invention are expected to be useful in targeted cancer therapy.

The invention thus relates in a first aspect (aspect A) to compounds of formula I

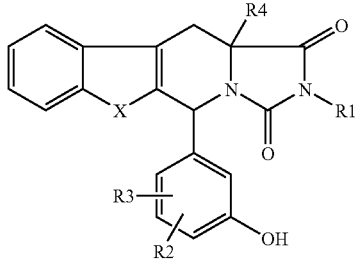

in which
R1 is 1-4C-alkyl, 3-7C-cycloalkyl, 3-7C-cycloalkyl-1-4C-alkyl, or 2-7C-alkyl substituted by R11, in which
R11 is —N(R111)R112, in which
R111 is hydrogen, or 1-4C-alkyl,
R112 is hydrogen, or 1-4C-alkyl,
or R111 and R112 together and with inclusion of the nitrogen atom, to which they are bonded, form a ring Het, in which
Het is piperidinyl, morpholinyl, thiomorpholinyl, or pyrrolidinyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy,
either
X is NH, oxygen or sulphur, and
R4 is 1-4C-alkyl,
or
X is sulphur, and
R4 is hydrogen,
or
X is oxygen, and
R4 is hydrogen,
and the salts, stereoisomers and the salts of the stereoisomers of these compounds.

The invention further relates in a second aspect (aspect B), which is an embodiment of aspect a, to compounds of formula I,
in which
R1 is 1-4C-alkyl, 3-7C-cycloalkyl, 3-7C-cycloalkyl-1-4C-alkyl, or 2-7C-alkyl substituted by R11, in which
R11 is —N(R111)R112, in which
R111 is hydrogen, or 1-4C-alkyl,
R112 is hydrogen, or 1-4C-alkyl,
or R111 and R112 together and with inclusion of the nitrogen atom, to which they are bonded, form a ring Het, in which
Het is piperidinyl, morpholinyl, thiomorpholinyl, or pyrrolidinyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy,
X is NH, oxygen or sulphur,
R4 is 1-4C-alkyl,
and the salts, stereoisomers and the salts of the stereoisomers of these compounds.

The invention further relates in a third aspect (aspect C), which is an embodiment of aspect a, to compounds of formula I, in which R1 is 1-4C-alkyl, 3-7C-cycloalkyl, 3-7C-cycloalkyl-1-4C-alkyl, or 2-7C-alkyl substituted by R11, in which R11 is —N(R111)R112, in which R111 is hydrogen, or 1-4C-alkyl, R112 is hydrogen, or 1-4C-alkyl, or R111 and R112 together and with inclusion of the nitrogen atom, to which they are bonded, form a ring Het, in which Het is piperidinyl, morpholinyl, thiomorpholinyl, or pyrrolidinyl, R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy, R3 is hydrogen, or 1-4C-alkoxy, X is sulphur, R4 is hydrogen, and the salts, stereoisomers and the salts of the stereoisomers of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

2-7C-Alkyl is a straight-chain or branched alkyl radical having 2 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl and ethyl radicals.

3-7C-Cycloalkyl stands for cyclopropyl, cyclobutyl, cyclopentyl, cyclohexyl and cycloheptyl, of which cyclopropyl, cyclopentyl and cyclohexyl are in particular to be mentioned.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the 3-7C-cycloalkylmethyl radicals, in particular the cyclopropylmethyl and the cyclopentylmethyl radical, and the cyclohexylethyl radical.

Halogen within the meaning of the present invention is iodine or, in particular, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radicals.

1-4C-Alkoxy-2-4C-alkoxy represents one of the abovementioned 2-4C-alkoxy radicals, which is substituted by one of the abovementioned 1-4C-alkoxy radicals. Examples which may be mentioned are the 2-methoxyethoxy, 2-ethoxyethoxy and the 2-isopropoxyethoxy radicals.

Hydroxy-2-4C-alkoxy represents one of the abovementioned 2-4C-alkoxy radicals, which is substituted by a hydroxyl radical. Examples which may be mentioned are the 2-hydroxyethoxy and the 3-hydroxypropoxy radicals.

3-7C-Cycloalkoxy stands for cyclopropyloxy, cyclobutyloxy, cyclopentyloxy, cyclohexyloxy or cycloheptyloxy, of which cyclopropyloxy, cyclopentyloxy and cyclohexyloxy are in particular to be mentioned.

3-7C-Cycloalkyl-1-4C-alkoxy stands for one of the abovementioned 1-4C-alkoxy radicals substituted by one of the abovementioned 3-7C-cycloalkyl radicals. Examples which may be mentioned are the 3-7C-cycloalkylmethoxy radicals, such as cyclopropylmethoxy, cyclobutylmethoxy, cyclopentylmethoxy, cyclohexylmethoxy or cycloheptylmethoxy, of which cyclopropylmethoxy or cyclopentylmethoxy are in particular to be mentioned.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds of formula I according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

The substituents R2 and R3 of compounds of formula I can be attached in the ortho, meta or para position with respect to the binding position in which the phenyl ring is bonded to the scaffold, whereby preference is given to the attachement in the meta or para position.

The compounds of formula I are chiral compounds having chiral centers in positions 3a and 10.

Numbering:

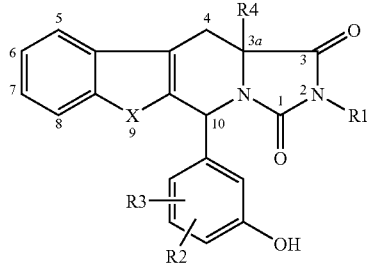

(I)

The invention includes all conceivable stereoisomers, like e.g. diastereomers and enantiomers, in substantially pure form as well as in any mixing ratio, including the racemates.

Preference is given hereby to compounds of formula I, which have with respect to the positions 3a and 10 the same configuration as shown in formula I*.

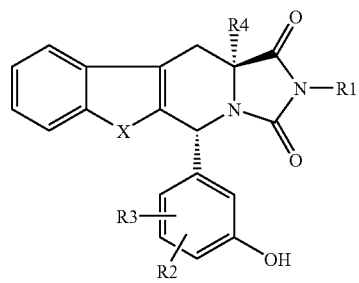

(I*)

If, for example, in compounds of formula I* R4 has the meaning methyl or hydrogen, then the configuration—according to the rules of Cahn, Ingold and Prelog—is S in the 3a position and R in the 10 position.

Furthermore, compounds of the formula I also worthy to be mentioned are those which have, with respect to the positions 3a and 10, the same configuration as shown in formula I**:

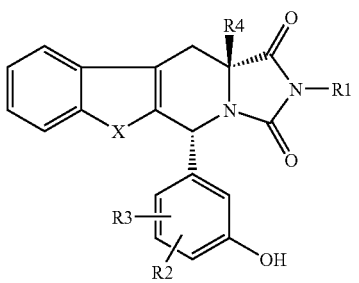

(I**)

If, for example, in compounds of formula I** R4 has the meaning methyl or hydrogen, then the configuration—according to the rules of Cahn, Ingold and Prelog—is R in the 3a position and R in the 10 position.

Further on, compounds of the formula I also to be mentioned are those which have, with respect to the positions 3a and 10, the same configuration as shown in formula I* or I**:

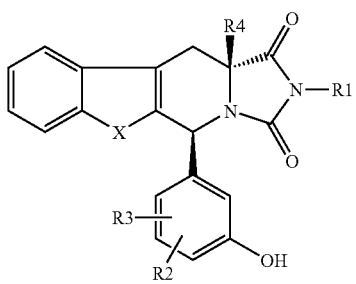

(I***)

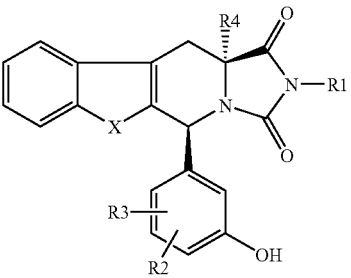

(I****)

If, for example, in compounds of formula I*** R4 has the meaning methyl or hydrogen, then the configuration—according to the rules of Cahn, Ingold and Prelog—is R in the 3a position and S in the 10 position.

If, for example, in compounds of formula I**** R4 has the meaning methyl or hydrogen, then the configuration—according to the rules of Cahn, Ingold and Prelog—is S in the 3a position and S in the 10 position.

In general, enantiomerically pure compounds of this invention can be prepared according to art-known processes, such as e.g. via asymmetric syntheses, for example by preparation and separation of appropriate diastereoisomeric compounds; by chromatographic separation on chiral separating columns; by means of salt formation of the racemic compounds with optically active acids or bases, subsequent resolution of the salts and release of the desired compound from the salt; by derivatization with chiral auxiliary reagents, subsequent diastereomer separation and removal of the chiral auxiliary group; or by (fractional) crystallization from a suitable solvent.

Preferably, enantiomerically pure compounds can be obtained starting from known enantiomerically pure starting compounds via synthesis of diastereomeric intermediates which can be separated by known methods (e.g. by chromatographic separation or crystallization).

In the context of this invention, hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. Inhibition of cell proliferation and analogous terms is used to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some proffered embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and tissue invasion and metastasis.

Inducer of apoptosis and analogous terms are used to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily be coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic and analogous terms is used in a more general sense to identify compounds which kill cells by various mechanisms, including the induction of apoptosis/programmed cell death in a cell cycle dependent or cell-cycle independent manner.

Cell cycle specific and analogous terms are used to identify a compound as inducing apoptosis only in continuously proliferating cells actively passing a specific phase of the cell cycle, but not in resting, non-dividing cells. Continuously proliferating cells are typical for diseases like cancer and characterized by cells in all phases of the cell division cycle, namely in the G ("gap") 1, S ("DNA synthesis"), G2 and M ("mitosis") phase.

Compounds according to aspect A of this invention more worthy to be mentioned are those compounds of formula I, in which
R1 is 1-2C-alkyl, cyclopropyl, cyclopropylmethyl, or 2-4C-alkyl substituted by R11, in which
R11 is —N(R111)R112, in which
R111 is 1-2C-alkyl,
R112 is 1-2C-alkyl,
or R111 and R112 together and with inclusion of the nitrogen atom, to which they are bonded, form a ring Het, in which Het is piperidinyl, morpholinyl, thiomorpholinyl, or pyrrolidinyl,
R2 is hydrogen,
R3 is hydrogen,
either
X is NH, oxygen or sulphur, and
R4 is methyl,
or
X is sulphur, and
R4 is hydrogen,
or
X is oxygen, and
R4 is hydrogen,
and the salts, stereoisomers and the salts of the stereoisomers of these compounds.

Compounds according to aspect A of this invention in particular worthy to be mentioned are those compounds of formula I which are from formula I* as shown below,
in which
R1 is methyl, ethyl, or ethyl substituted by R11, in which
R11 is —N(R111)R112, in which
R111 is methyl,
R112 is methyl,
or R111 and R112 together and with inclusion of the nitrogen atom, to which they are bonded, form a ring Het, in which Het is morpholinyl,
R2 is hydrogen,
R3 is hydrogen,
either
X is NH, oxygen or sulphur, and
R4 is methyl,
or
X is sulphur, and
R4 is hydrogen,
or
X is oxygen, and
R4 is hydrogen,
and the salts of these compounds.

In one embodiment, compounds according to aspect A of this invention in more particular worthy to be mentioned are those compounds of formula I which are from formula I* as shown below,
in which
R1 is methyl, or ethyl substituted by R11, in which
R11 is —N(R111)R112, in which
R111 is methyl,
R112 is methyl,
R2 is hydrogen,
R3 is hydrogen,
X is NH, and
R4 is methyl,
or
X is sulphur, and
R4 is methyl,
or
X is oxygen, and
R4 is methyl,
and the salts of these compounds.

In another embodiment, compounds according to aspect A of this invention in more particular worthy to be mentioned are those compounds of formula I which are from formula I* as shown below,
in which
R1 is methyl, or ethyl substituted by R11, in which
R11 is —N(R111)R112, in which
R111 is methyl,
R112 is methyl,
R2 is hydrogen,
R3 is hydrogen,
either
X is sulphur, and
R4 is hydrogen,
or
X is oxygen, and
R4 is hydrogen,
and the salts of these compounds.

In one embodiment, compounds according to aspect A of this invention to be emphasized are those compounds of formula I which are from formula I* as shown below,
in which
R1 is methyl,
R2 is hydrogen,
R3 is hydrogen,
either
X is NH, and
R4 is methyl,
or
X is sulphur, and
R4 is methyl,
or X is oxygen, and
R4 is methyl,
and the salts of these compounds.

In another embodiment, compounds according to aspect A of this invention to be emphasized are those compounds of formula I which are from formula I* as shown below,
in which
R1 is methyl,
R2 is hydrogen,
R3 is hydrogen,
either
X is sulphur, and
R4 is hydrogen,
or
X is oxygen, and
R4 is hydrogen,
and the salts of these compounds.

Compounds according to aspect B of this invention more worthy to be mentioned are those compounds of formula I,
in which
R1 is 1-4C-alkyl, 3-5C-cycloalkyl, 3-5C-cycloalkyl-1-4C-alkyl, or 2-7C-alkyl substituted by R11, in which
R11 is —N(R111)R112, in which
R111 is hydrogen,
R112 is hydrogen,
R2 is hydrogen,
R3 is hydrogen,
X is NH, oxygen or sulphur,
R4 is methyl,
and the salts, stereoisomers and the salts of the stereoisomers of these compounds.

Compounds according to aspect B of this invention in particular worthy to be mentioned are those compounds of formula I,
in which
R1 is 1-2C-alkyl, cyclopropyl, cyclopropylmethyl, or 2-amino-ethyl,
R2 is hydrogen,
R3 is hydrogen,
X is NH, oxygen or sulphur,
R4 is methyl,
and the salts, stereoisomers and the salts of the stereoisomers of these compounds.

Compounds according to aspect B of this invention in more particular worthy to be mentioned are those compounds of formula I,
in which
R1 is methyl, ethyl, or cyclopropyl,
R2 is hydrogen,
R3 is hydrogen,
X is NH, oxygen or sulphur,
R4 is methyl,
and the salts, stereoisomers and the salts of the stereoisomers of these compounds.

Compounds according to aspect B of this invention to be emphasized are those compounds of formula I,
in which
R1 is methyl,
R2 is hydrogen,
R3 is hydrogen,
X is NH, oxygen or sulphur,
R4 is methyl,
and the salts, stereoisomers and the salts of the stereoisomers of these compounds.

Compounds according to aspect C of this invention more worthy to be mentioned are those compounds of formula I,
in which
R1 is 1-4C-alkyl, 3-5C-cycloalkyl, 3-5C-cycloalkyl-1-4C-alkyl, or 2-7C-alkyl substituted by R11, in which
R11 is —N(R111)R112, in which
R111 is hydrogen,
R112 is hydrogen,
R2 is hydrogen,
R3 is hydrogen,
X is sulphur,
R4 is hydrogen,
and the salts, stereoisomers and the salts of the stereoisomers of these compounds.

Compounds according to aspect C of this invention in particular worthy to be mentioned are those compounds of formula I,
in which
R1 is 1-2C-alkyl, cyclopropyl, cyclopropylmethyl, or 2-amino-ethyl,
R2 is hydrogen,
R3 is hydrogen,
X is sulphur,
R4 is hydrogen,
and the salts, stereoisomers and the salts of the stereoisomers of these compounds.

Compounds according to aspect C of this invention in more particular worthy to be mentioned are those compounds of formula I,
in which
R1 is methyl, ethyl, or cyclopropyl,
R2 is hydrogen,
R3 is hydrogen,
X is sulphur,
R4 is hydrogen,
and the salts, stereoisomers and the salts of the stereoisomers of these compounds.

A special interest in the compounds according to this invention refers to those compounds of formula I which are included—within the scope of this invention—by one or, when possible, by more of the following special embodiments:

A special embodiment (embodiment 1) of the compounds of formula I according to this invention refers to those compounds of formula I, in which
R1 is methyl.

Another special embodiment (embodiment 2) of the compounds of formula I according to this invention refers to those compounds of formula I, in which
R2 is hydrogen.

Another special embodiment (embodiment 3) of the compounds of formula I according to this invention refers to those compounds of formula I, in which
R3 is hydrogen.

Another special embodiment (embodiment 4) of the compounds of formula I according to this invention refers to those compounds of formula I, in which
R2 and R3 are both hydrogen.

Another special embodiment (embodiment 5) of the compounds of formula I according to this invention refers to those compounds which are from formula I* as shown above.

Another special embodiment (embodiment 6) of the compounds of formula I according to this invention refers to those compounds of formula I, in which
R4 is methyl.

Another special embodiment (embodiment 7) of the compounds of formula I according to this invention refers to those compounds of formula I, in which
X is NH, and R4 is methyl.

Another special embodiment (embodiment 8) of the compounds of formula I according to this invention refers to those compounds of formula I, in which
X is oxygen, and R4 is methyl.

Another special embodiment (embodiment 9) of the compounds of formula I according to this invention refers to those compounds of formula I, in which
X is sulphur, and R4 is methyl.

Another special embodiment (embodiment 10) of the compounds of formula I according to this invention refers to those compounds of formula I, in which
R4 is hydrogen.

Another special embodiment (embodiment 11) of the compounds of formula I according to this invention refers to those compounds of formula I, in which
X is sulphur, and R4 is hydrogen.

Another special embodiment (embodiment 12) of the compounds of formula I according to this invention refers to those compounds of formula I, in which
X is oxygen, and R4 is hydrogen.

Another special embodiment (embodiment 13) of the compounds of formula I according to this invention refers to those compounds of formula I, in which
R1 is 2-(N,N-dimethylamino)-ethyl.

A particular special embodiment (embodiment 14) of the compounds of formula I according to this invention refers to those compounds of formula I*, in which
X is NH, R1 is 2-(N,N-dimethylamino)-ethyl, and R4 is methyl.

Another particular special embodiment (embodiment 15) of the compounds of formula I according to this invention refers to those compounds of formula I*, in which
X is sulphur, R1 is 2-(N,N-dimethylamino)-ethyl, and R4 is methyl.

Another particular special embodiment (embodiment 16) of the compounds of formula I according to this invention refers to those compounds of formula I*, in which
X is sulphur, R1 is 2-(N,N-dimethylamino)-ethyl, and R4 is hydrogen.

A further particular special embodiment (embodiment 13) of the compounds of formula I according to this invention refers to those compounds of formula I*, in which
X is NH, R1 is methyl, and R4 is methyl.

Another further particular special embodiment (embodiment 14) of the compounds of formula I according to this invention refers to those compounds of formula I*, in which
X is sulphur, R1 is methyl, and R4 is methyl.

Another further particular special embodiment (embodiment 15) of the compounds of formula I according to this invention refers to those compounds of formula I*, in which
X is sulphur, R1 is methyl, and R4 is hydrogen.

As exemplary compounds according to this invention the following compounds of formula I* in which R2 and R3 are both hydrogen, can be mentioned by means of the substituent meanings for R1, R4 and X in the following Table 1.

TABLE 1

| No. | R1 | R4 | X |
| --- | --- | --- | --- |
| 1.1 | —$CH_3$ | —$CH_3$ | NH |
| 1.2 | —$CH_3$ | —$CH_3$ | S |
| 1.3 | —$CH_2CH_2$—$N(CH_3)_2$ | —$CH_3$ | NH |
| 1.4 | —$CH_2CH_2$—$N(CH_3)_2$ | —$CH_3$ | S |
| 1.5 | —$CH_3$ | H | S |
| 1.6 | —$CH_2CH_2$—$N(CH_3)_2$ | H | S |

The compounds according to the invention can be prepared e.g. as described exemplarily as follows and according to the following specified reaction steps, or, particularly, in a manner as described by way of example in the following examples, or analogously or similarly thereto according to preparation procedures or synthesis strategies known to the person skilled in the art.

As shown in the synthesis route outlined in scheme 1 below, compounds of formula IV, in which X and R4 have the meanings given above, are condensed and cyclized in a Pictet-Spengler reaction with benzaldehydes of formula III, in which R2 and R3 have the meanings mentioned above, to give the corresponding compounds of formulae IIa and/or IIb mostly as a mixture. Said Pictet-Spengler reaction can be carried out as it is known to the skilled person or as described in the following examples, advantageously in the presence of a suitable acid as a catalyst or promotor (e.g. trifluoroacetic acid) in a suitable solvent, for example toluene, at elevated temperature.

Compounds of formula IV, in which X and R4 have the meanings given above, are known or can be obtained in a known manner, e.g. by esterification of corresponding compounds of formula V which are known or obtainable in a known manner. Thus, e.g. 2-amino-3-(1H-indol-3-yl)-2-methyl-propionic acid methyl ester is commercially available. Further on, (R)-2-amino-3-(benzothiophen-3-yl)-propionic acid methyl ester is obtained from D-thiotryptophan by esterification reaction. Said esterification reaction can be carried out in a manner habitual per se to the skilled person, e.g. via an appropriate corresponding activated form of the acid, such as, for example, the corresponding acid chloride—obtainable with the aid of thionyl chloride or the like—which is reacted with the corresponding alcohol, preferably methanol. D-Thiotryptophan is known or can be obtained in a known manner.

Moreover, compounds of formula IV or V, in which R4 is 1-4C-alkyl, particularly methyl can be obtained by asymmetric synthesis. Thus, e.g. enantiomerically pure compounds of formula IV or V, in which R4 is 1-4C-alkyl, particularly methyl, can be obtained from the corresponding compounds of the formula IV or V, respectively, in which R4 is hydrogen, by art-known stereoselective alkylation reaction, such as e.g. (S)-α-methyltryptophan can be obtained from L-tryptophane as described in J. Org. Chem. 1995, 60, 5719-5720.

Compounds of formula III are known or can be obtained in a known manner.

Reaction scheme 1:

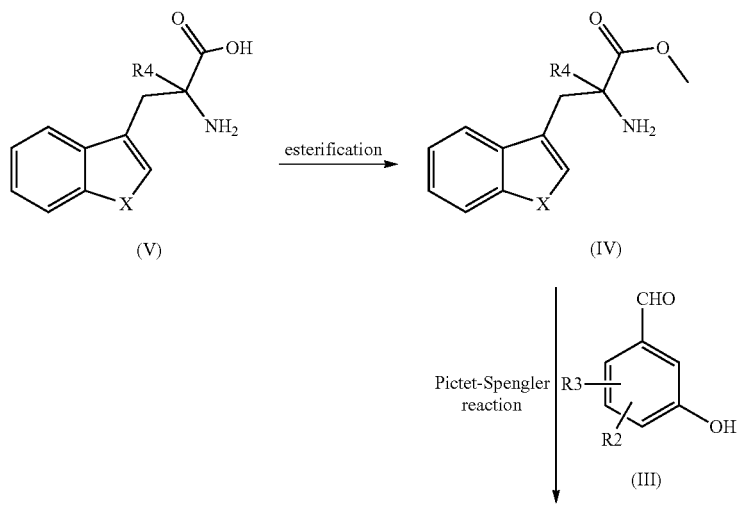

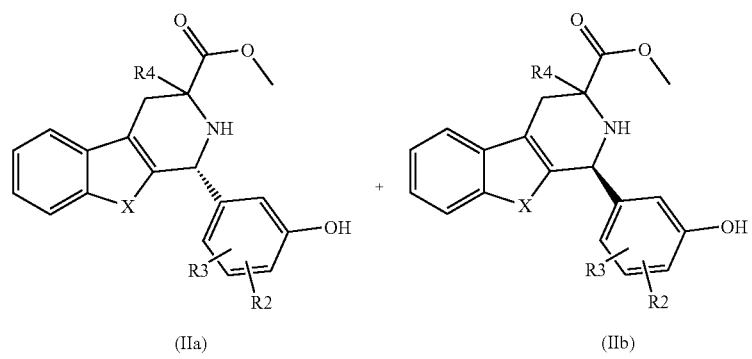

Optional separation of diastereomers by column chromatography

The compounds of formula IV can be employed in the above-mentioned Pictet-Spengler reaction as racemate or enantiomerically pure compounds. Depending thereon, the mixture obtained can contain the compounds of formulae IIa and IIb as diastereomers or as diastereomeric racemate. Said mixture can be optionally separated in a manner habitual per se to the skilled person, such as e.g. diastereomeric compounds of formulae IIa and IIb can be separated by column chromatography. If appropriate, said mixture can be also used in the next step without further separation of the diastereoisomers. Then, separation of diastereomers can be carried out subsequently to one of the following steps.

When the compounds of formula IV, in which R4 is 1-4C-alkyl, particularly methyl, are employed as racemic mixture in the abovementioned Pictet-Spengler reaction, the racemate comprising the enantiomeric compounds of formulae IIa' and IIb', in each of which R4 R4 is 1-4C-alkyl, particularly methyl, can be obtained preferentially or in excess from said reaction.

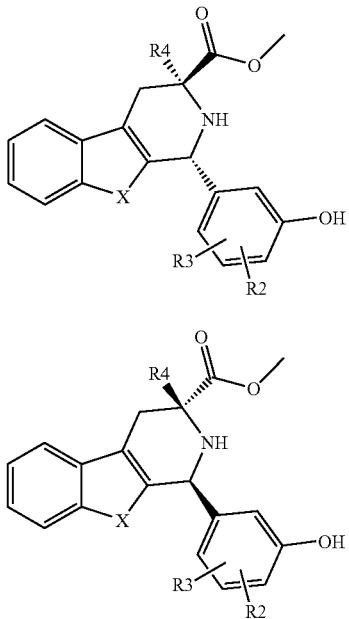
(IIa')

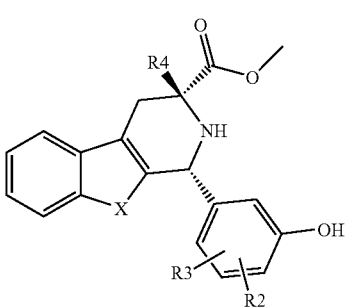
(IIb')

(IIa")

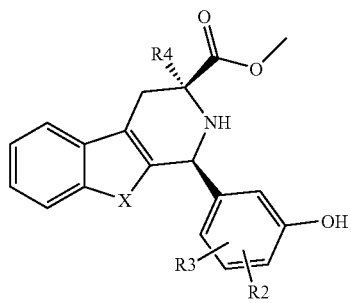
(IIb")

Starting from the appropriate pure enantiomers of the compounds of formula IV, in which R4 is 1-4C-alkyl, particularly methyl, corresponding compounds of either formula IIa' or formula IIb' (depending from the configuration of the starting compound of formula IV) can be obtained preferentially. Thus, e.g. when (S)-α-methyltryptophan methyl ester [i.e. (S)-2-amino-3-(1H-indol-3-yl)-2-methyl-propionic acid methyl ester] is employed in the abovementioned Pictet-Spengler reaction, corresponding compounds of formula IIa', in which X is NH and R4 is methyl, are obtained preferentially.

When the compounds of formula IV, in which R4 is hydrogen, are employed as racemic mixture in the abovementioned Pictet-Spengler reaction, the racemate comprising the enantiomeric compounds of formulae IIa" and IIb", in each of which R4 is hydrgen, can be obtained preferentially or in excess from said reaction.

Starting from the appropriate pure enantiomers of the compounds of formula IV, in which R4 is hydrogen, corresponding compounds of either formula IIa" or formula IIb" (depending from the configuration of the starting compound of formula IV) can be obtained preferentially. Thus, e.g. when (R)-2-amino-3-(benzothiophen-3-yl)-propionic acid methyl ester is employed in the abovementioned Pictet-Spengler reaction, corresponding compounds of formula IIa", in which X is S and R4 is hydrogen, are obtained preferentially.

Compounds of formula IIa' or IIb', in each of which R4 is 1-4C-alkyl, particularly methyl, e.g. in enantiomerically pure form or as racemic mixture or with corresponding diastereomers co-generated in the Pictet-Spengler reaction above, can be reacted with isocyanates of formula R1-N=C=O or with corresponding activated carbamic acid esters, such as, for example, N-hydroxysuccinimid-activated urethanes, like e.g. $H_3C$—NH—C(O)—OR, in which R is 1N-succinimidyl, in a Hydantoin synthesis as shown in reaction scheme 2 to give the corresponding desired hydantoins of formula I* (from compounds of formula IIa') or I*** (from compounds of formula IIb'), in each of which R4 is 1-4C-alkyl, particularly methyl. Said Hydantoin synthesis can be performed in an art-known manner or as described in the following examples, e.g. in the presence of microwaves.

When the compounds of formulae I* and I*** are obtained as racemic mixture, the enantiomerically pure compounds may be accessible by art-known separation techniques, such as e.g. those described above or as specified in the following examples.

Isocyanates of formula R1-N=C=O, in which R1 has the meanings given above, are known or can be obtained according to known procedures. Thus, e.g. compounds of formula R1-N=C=O, in which R1 is 2-7C-alkyl substituted by —N(R111)R112, can be obtained from compounds of formula R1-N=C=O, in which R1 is 2-7C-alkyl substituted by a suitable leaving group, such as e.g. bromine, by nucleophilic substitution reaction with corresponding amines of formula HN(R111)R112 in a manner habitual per se to the skilled person or similarly as described by way of example in the following example.

Reaction scheme 2:

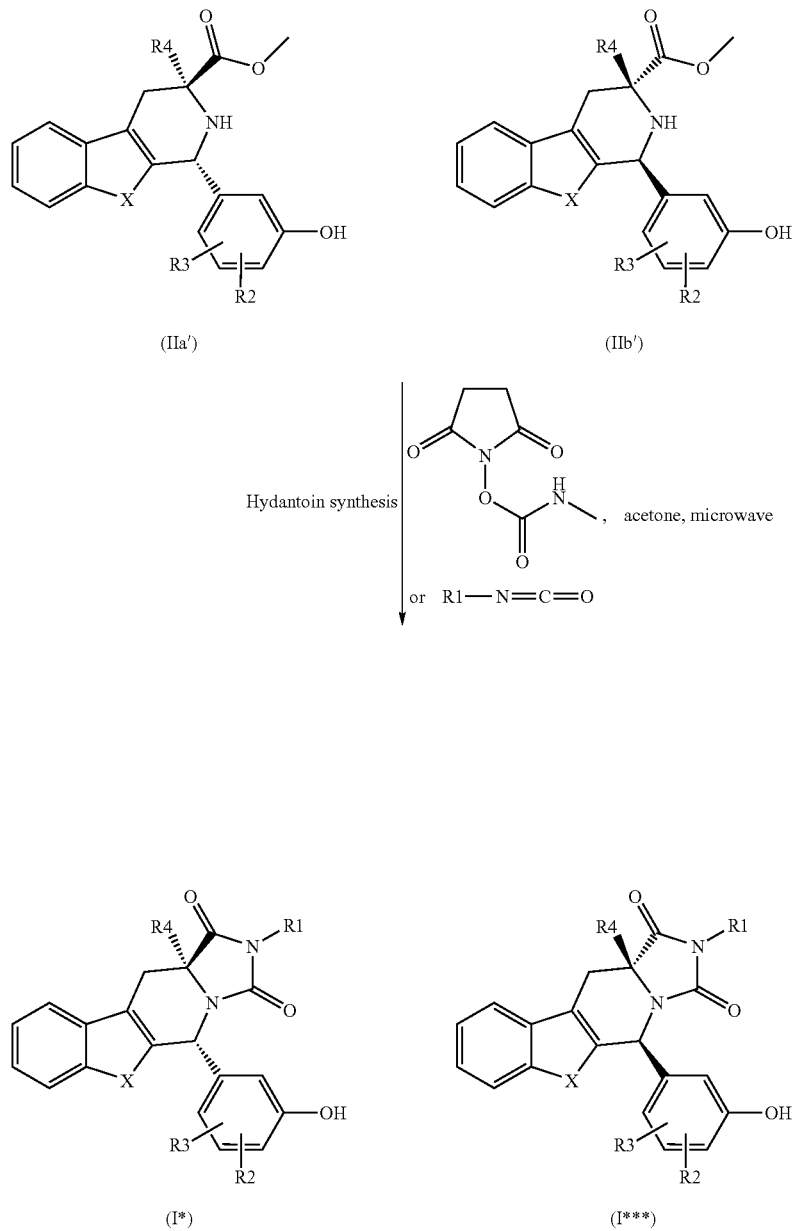

Compounds of formula IIa" or IIb", in each of which R4 is hydrogen, e.g. in enantiomerically pure form or as racemic mixture or with corresponding diastereomers co-generated in the Pictet-Spengler reaction above, can be reacted with isocyanates of formula R1-N=C=O or with corresponding activated carbamic acid esters, such as, for example, N-hydroxysuccinimid-activated urethanes, like e.g. H$_3$C—NH—C(O)—OR, in which R is 1N-succinimidyl, in a Hydantoin synthesis as shown In reaction scheme 3 to give the corresponding desired hydantoins of formula I (from compounds of formula IIa") or I** (from compounds of formula IIb"), in each of which R4 is hydrogen. Said Hydantoin synthesis can be performed in an art-known manner or as described in the following examples, e.g. in the presence of microwaves.

Reaction scheme 3:

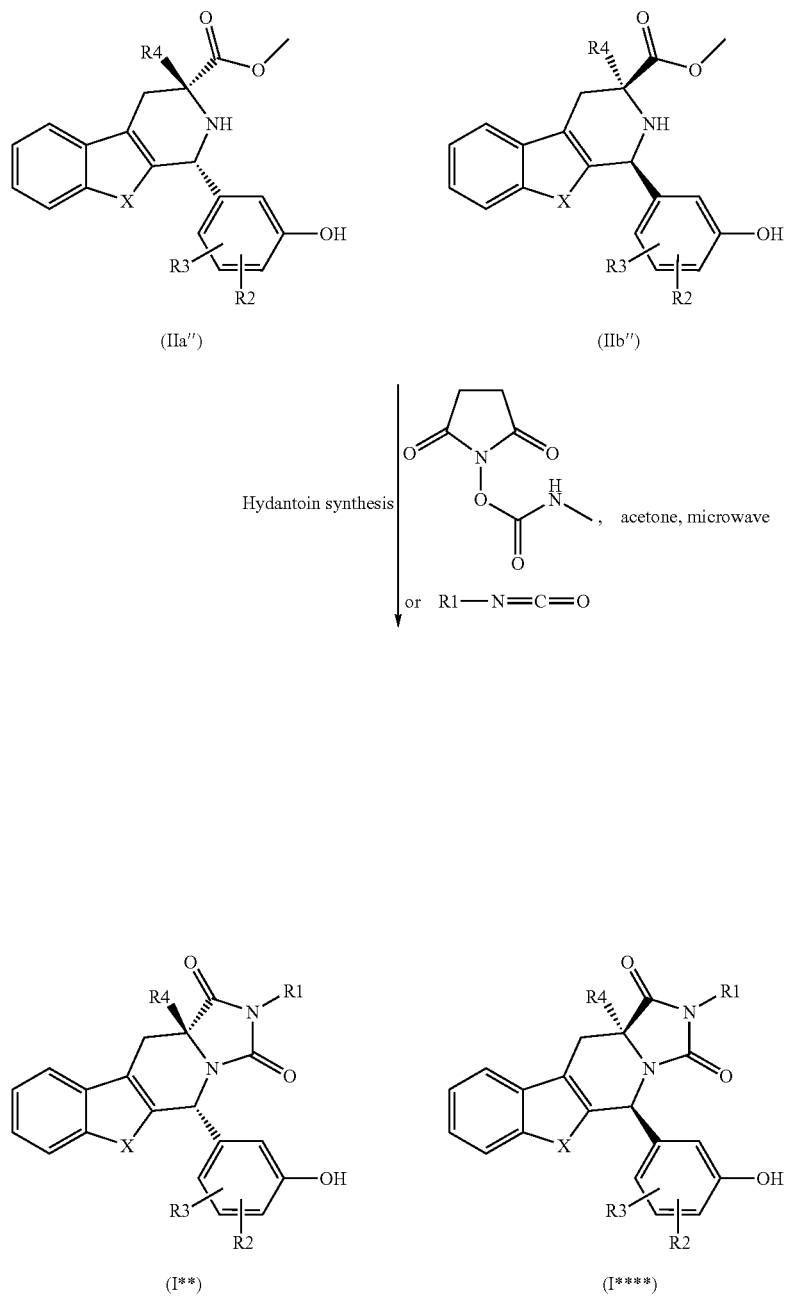

Optionally, the configuration of the chiral carbon atom 3a of compounds of formula I, in which R4 is hydrogen, can be epimerized via deprotonation/reprotonation with the aid of a suitable base such as e.g. potassium carbonate in a suitable solvent such as e.g. acetonitrile.

Thus e.g. as shown in reaction scheme 4, compounds of formula I**, in which X, R1, R2 and R3 have the meanings indicated above and R4 is hydrogen, can be converted into corresponding compounds of formula I*.

Reaction scheme 4:

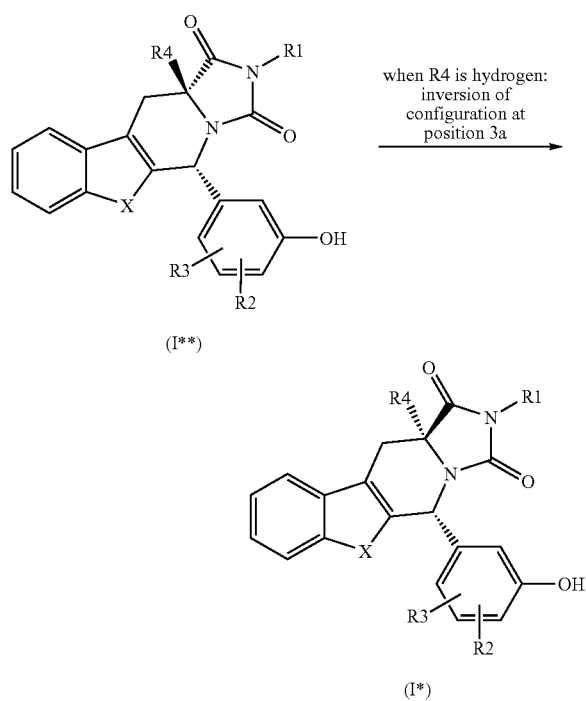

Likewise, depending on the reaction conditions used, at least partial epimerization of the configuration of the CH atom adjacent to the carbonyl group can take place in the aforementioned Hydantoin synthesis.

When the compounds of formulae I* and I*** are obtained as racemic mixture, the corresponding enantiomerically pure compounds may be accessible by art-known separation techniques, such as e.g. those described above.

Optionally, compounds of the formula I can be converted into their salts, or, optionally, salts of the compounds of the formula I can be converted into the free compounds.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts can be obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts can be obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the appended claims.

The following examples serve to illustrate the invention further without restricting it. Likewise, further compounds according to this invention, whose preparation is not explicitly described, can be prepared in an analogous or similar manner or in a manner familiar per se to the person skilled in the art using customary process techniques.

Any or all of the compounds of formula I according to this invention which are mentioned as final compounds in the following examples, and particularly those enantiomers thereof having the formula I*, as well as the salts of these compounds and enantiomers, are a preferred subject of the present invention.

In the examples, m.p. stands for melting point, h for hour(s), min for minutes, conc. for concentrated, calc. for calculated, fnd. for found, M for molecular ion in mass spectrometry, and other abrevations have their meanings customary per se to the skilled person.

According to common practice in stereochemistry, the symbols RS and SR are used to denote the specific configuration of each of the indicated chiral centers of a racemate. In more detail, for example, the term "(3aSR,10RS)" stands for a racemate comprising the one enantiomer having the configuration (3aS,10R) and the other enantiomer having the configuration (3aR,10S).

EXAMPLES

Final Compounds 1. (±)-(3aSR,10RS)-10-(3-Hydroxy-phenyl)-2,3a-dimethyl-3a,4,9,10-tetrahydro-2,9,10a-triaza-cyclopenty[b]fluorene-1,3-dione To a suspension of 250 mg (740 μmol) (1RS,3SR)-1-(3-hydroxy-phenyl)-3-methyl-2,3,4,9-tetrahydro-1H-β-carboline-3-carboxylic acid methyl ester (compound A1) in 4 ml acteonitrile and 1 ml water are added 511 mg (3 mmol) N-succinimidyl-N-methylcarbamate. The mixture is heated to 150° C. for 5 min using a microwave reactor. The solvents are removed under reduced pressure. The residue is dissolved in ethyl acetate and the organic layer is washed with water. The solution is dried with magnesium sulfate and the solvent is removed under reduced pressure. After column chromatography (toluene, ethyl acetate 4:1), 68 mg (25%) of the title compound are obtained as a white solid (m.p.: 299-305° C.; m/z (MH$^+$)=362.2).

2. (3aS,10R)-10-(3-Hydroxy-phenyl)-2,3a-dimethyl-3a,4,9,10-tetrahydro-2,9,10a-triaza-cyclopenty[b]fluorene-1,3-dione Starting from the corresponding racemate (Example 1) the title compound as well as (3aR,10S)-10-(3-hydroxy-phenyl)-2,3a-dimethyl-3a,4,9,10-tetrahydro-2,9,10a-triaza-cyclopenty[b]fluorene-1,3-dione can be obtained by chromatographical separation using the following conditions: Column: 250×20 mm Chiralpak OD-I 20 µm; Mobile phase: 80/20 CO2/MeOH (sample in DMSO/MeOH 50/50); Flow rate: 60 ml/min; Detection: UV 295 nm; Temperature: 25° C.; Outlet pressure: 150 bar.

Using these conditions, the title compound is obtained as second eluated compound.

3. (3aS,10R)-10-(3-Hydroxy-phenyl)-2-methyl-4,10-dihydro-3aH-9-thia-2,10-diaza-cyclopenta[b]fluorene-1,3-dione Crude (3aR,10R)-10-(3-hydroxy-phenyl)-2-methyl-4,10-dihydro-3aH-9-thia-2,10-diaza-cyclo-penta[b]-fluorene-1,3-dione (compound A3) obtainable as described below is dissolved in 10 ml of acetonitrile. 815 mg (5.90 mmol) of potassium carbonate are added and the suspension is heated to reflux for 2 h. The solvent is removed under reduced pressure. Water and ethyl acetate are added and the aqueous layer is washed with ethyl acetate. The combined organic phases are washed with brine and dried with magnesium sulfate. The solvent is removed under reduced pressure. After the addition of diisopropyl ether to the residue, 48 mg (22%) of the title compound can be obtained as white crystals. (m.p. 213.3° C.-216.4° C., m/z (MH$^+$)=365.1).

4. (3aS,10R)-2-Butyl-10-(3-hydroxy-phenyl)-4,10-dihydro-3aH-9-thia-2,10a-diaza-cyclopenta[b]fluorene-1,3-dione The title compound is prepared similarly as described to attain to Example 3 using butyl isocyanate instead of N-succinimidyl-N-methylcarbamate.

C,23; H,22; N,2; O,3; S, (calc.: 406.51). Fnd.: m/z (MH$^+$)= 362.2.

5. (3aSR,10RS)-10-(3-Hydroxy-phenyl)-2,3a-dimethyl-4,10-dihydro-3aH-9-thia-2,10a-diaza-cyclopenta[b]fluorene-1,3-dione The title compound is prepared similarly as described to attain to Example 1 using compound A5 as starting material
C,21; H,18; N,2; O,3; S, (calc.: 378.45). Fnd.: m/z. (MH$^+$)= 379.0.

6. (3aS,10R)-10-(3-Hydroxy-phenyl)-2,3a-dimethyl-4,10-dihydro-3aH-9-thia-2,10a-diaza-cyclopenta[b]fluorene-1,3-dione Starting from the corresponding racemate (Example 5) the title compound may be obtained by chromatographical separation.

7. (3aS,10RS)-2-(2-Dimethylamino-ethyl)-10-(3-hydroxy-phenyl)-3a-methyl-3a,4,9,10-tetrahydro-2,9,10a-triaza-cyclopenty[b]fluorene-1,3-dione The title compound may be prepared using similar procedures to those described in Example 1, but with choice of compound A6 as starting material.

8. (3aS,10R)-2-(2-Dimethylamino-ethyl)-10-(3-hydroxy-phenyl)-3a-methyl-3a,4,9,10-tetrahydro-2,9,10a-triaza-cyclopenty[b]fluorene-1,3-dione Starting from the corresponding racemate (Example 7) the title compound may be obtained by chromatographical separation.

9. (3aS,10R)-2-(2-Dimethylamino-ethyl)-10-(3-hydroxy-phenyl)-4,10-dihydro-3aH-9-thia-2,10-diaza-cyclopenta[b]fluorene-1,3-dione The title compound may be prepared using similar procedures to those described to attain to Example 3, but with choice of compound A6 as starting material.

10. (3aSR,10RS)-2-(2-Dimethylamino-ethyl)-10-(3-hydroxy-phenyl)-3a-methyl-4,10-dihydro-3aH-9-thia-2,10a-diaza-cyclopenta[b]fluorene-1,3-dione The title compound may be prepared using similar procedures to those described to attain to Example 5, but with choice of compound A6 as starting material.

11. (3aS,10R)-2-(2-Dimethylamino-ethyl)-10-(3-hydroxy-phenyl)-3a-methyl-4,10-dihydro-3aH-9-thia-2,10a-diaza-cyclopenta[b]fluorene-1,3-dione Starting from the corresponding racemate (Example 10) the title compound may be obtained by chromatographical separation.

Starting Compounds

A1. (±)-(1RS,3SR)-1-(3-Hydroxy-phenyl)-3-methyl-2,3,4,9-tetrahydro-1H-β-carboline-3-carboxylic acid methyl ester 1.00 g (4.30 mmol) of the commercially available 2-amino-3-(1H-indol-3-yl)-2-methyl-propionic acid methyl ester are reacted with 600 mg (4.73 mmol) 3-hydroxy-benzaldehyde in the presence of trifluoroacetic acid according to the Pictet-Spengler reaction. The resulting mixture of diastereomers is separated by column chromatography (toluene, ethyl acetate 4:1). 1.17 g (68%) of the title compound and 320 mg (14%) of (1SR,3SR)-1-(3-hydroxy-phenyl)-3-methyl-2,3,4,9-tetrahydro-1H-β-carboline-3-carboxylic acid methyl ester (compound A2) are obtained as white solids.

Compound A1: m.p.: 227.5° C.; m/z (MH$^+$): 337.0
Compound A2: m.p.: 221.5° C.; m/z (MH$^+$): 336.9

A3. (3aR,10R)-10-(3-Hydroxy-phenyl)-2-methyl-4,10-dihydro-3aH-9-thia-2,10-diaza-cyclopenta[b]fluorene-1,3-dione 405 mg (2.35 mmol) of N-succinimidyl-N-methyl carbamate are added to a solution of 200 mg (590 µmol) of (1R,3R)-1-(3-hydroxy-phenyl)-1,2,3,4-tetrahydro-benzo[4,5]thieno[2,3-c]pyridine-3-carboxylic acid methyl ester (compound

A4) in 4 ml of acetone. The mixture is heated to 150° C. for 5 min. using a microwave reactor. The solvent is removed under reduced pressure.

The crude product obtained can be used as starting material to obtain compound 3.

A4. (1R,3R)-1-(3-Hydroxy-phenyl)-1,2,3,4-tetrahydro-benzo[4,5]thieno[2,3-c]pyridine-3-carboxylic acid methyl ester 1.45 g (11.9 mmol) of 3-hydroxy benzaldehyde and 4.2 ml (54.6 mmol) of trifluoro acetic acid are added to a solution of 2.04 g (8.7 mmol) of 2-amino-3-benzo[b]thiophen-3-yl-propionic acid methyl ester (compound B1) in 20 ml of toluene. The solution is stirred at 40° C. over night. The mixture is washed with a saturated solution of sodium hydrogen carbonate. The aqueous layer is washed with ethyl acetate and the combined organic layers are washed with 5 M hydrochloric acid and dried with magnesium sulfate. 3.61 g of a brown oil are obtained as the crude product.

The title compound is separated from byproducts and from the resulting diastereomer by column chromatography (silica gel, toluene/ethyl acetate 9:1). 960 mg (32%) are obtained as a white solid (m.p. 282.9° C.-285.3° C., m/z (MH$^+$)=381.1).

A5. (±)-trans-1-(3-Hydroxyphenyl)-5-methyl-5-methoxycarbonyl-1,2,3,4-tetrahydrobenzo[4,5]-thieno[2,3]pyridine To a solution of 1.19 g of compound B2 in toluene 3-hydroxybenzaldehyde (0.80 g) and trifluoroacetic acid (2.30 mL) are added, and the mixture is stirred at 40° C. After 2 days the mixture is made alkaline with aqueous NaHCO$_3$ and is extracted with ethyl acetate (3×50 mL). The combined organic layer is washed with water, dried and concentrated. Column chromatography (toluene-acetone, 9:1) of the residue gives the two diastereomers of which the title compound is the faster migrating one (m.p. 214-215° C. (from ethyl acetate—light petroleum)).

A6. (2-isocyanato-ethyl)-dimethyl-amine 2.50 g 2-bromoethylisocyanate are dissolved in 20 ml dichloromethane. A weak flow of dimethylamine is bubbled through the solution for 3 hours.

The solvent is removed at reduced pressure. 1.9 g of the title compound are obtained as a colourless oil, which can be used without further purification (m/z (M$^+$)=114.1.

B1. 2-Amino-3-benzo[b]thiophen-3-yl-propionic acid methyl ester

A suspension of 5.00 g (22.6 mmol) H-β-(3-benzothienyl)-D-Ala-OH in 70 ml of methanol is cooled to 0° C. 8.3 ml (113 mmol) of thienyl chloride are added dropwise (the temperature rises up to 10° C. during the addition). The solution is stirred at 0° C. for 1 hour and at room temperature over night. The solvent is removed under reduced pressure and the residue is washed with a saturated solution of sodium hydrogen carbonate. The aqueous phase is extracted with ethyl acetate. The combined organic layers are washed with brine and dried with magnesium sulfate. The solvent is removed under reduced pressure. 5.37 g (quant.) of the title compound are obtained as a pale yellow oil (m/z (MH$^+$)=236.0).

B2. (±)-Methyl 2-amino-3-benzo[b]thiophene-3-yl-2-methyl-propionate

To a solution of potassium t-butoxide (4.82 g) in dry tetrahydrofuran (60 mL) cooled to −30° C. a solution of 6.85 g of (±)-2-(benzylidene-amino)-propionic acid methyl ester (compound C2) in tetrahydrofuran (20 mL) is added dropwise (compound C2 is prepared as described in J. W. Tilley, P. Levitan, R. W. Kierstead, J. Heterocycl. Chem., 16, 333 (1979) and P. Bey, J.-P. Vevert, V. Van Dorsselaer, M. Kolb, J. Org. Chem., 44, 2732 (1979)). The mixture is stirred at −30° C. for 30 minutes, then a solution of 7.85 g of compound C1 in tetrahydrofuran (20 mL) is added, and the mixture is stirred at the same temperature. When TLC (toluene-acetone, 95:5) indicates the disappearance of the starting material (cca 6 h), the mixture is diluted with dichloromethane, washed with water, dried and the solvent is evaporated. The residue is dissolved in dichloromethane (30 mL), cooled in an ice bath, and an ethereal solution of HCl is added to pH cca 1. The mixture is stirred for 1 h and the solvent is removed at reduced pressure. The residue is taken up in methanol, and is made alkaline with Amberlite IR 400 [OH$^-$] resin. The resin is filtered off, washed with methanol, and the filtrate is concentrated. Column chromatography of the residue (toluene-acetone, 4:1) affords the title compound (4.28 g, 48%) as a syrup, which crystallizes on standing. M.p. 44-45° C. (from ethyl acetate—light petroleum).

C1. 3-Chloromethyl-benzo[b]thiophene

The title compound is prepared following S. Avakian, J. Moss and G. J. Martin, J. Am. Chem. Soc., 70, 3075 (1948) and F. F. Blicke, D. G. Sheets, J. Am. Chem. Soc., 70, 3768 (1948).

A rapid stream of hydrogen chloride gas is bubbled through an intensely stirred mixture of benzothiophene (40.26 g), 36% aqueous formaldehyde (80 mL) and concentrated hydrochloric acid (20 mL) cooled in an ice bath. After 20 minutes the mixture is diluted with ice-water, and is extracted with dichloromethane (3×200 mL). The combined organic phase is washed with aqueous NaHCO$_3$, dried and the solvent is evaporated. Vacuum distillation of the residue affords the title compound (28.9 g, 52%) as the main fraction boiling at 128-132° C. (7.1 mbar), which crystallizes on standing.

Commercial Utility

The compounds according to the present invention have valuable pharmacological properties which can make them commercially applicable. Thus, for example, the compounds according to this invention can act as inhibitors of the mitotic kinesin Eg5 and these compounds are expected to be commercially applicable in the therapy of diseases responsive to the inhibition of this kinesin, such as e.g. those diseases mentioned below. Also, for example, the compounds according to this invention can display cell-cycle dependent, anti-proliferative and/or apoptosis inducing activity.

The mitotic kinesin Eg5 is an enzyme essential for the assembly and function of the bipolar mitotic spindle. Eg5 plays essential roles during all phases of mitosis. Drugs that perturb mitosis have proven clinically effective in the treatment of many cancers. Despite the diverse array of essential spindle proteins that could be exploited as targets for the discovery of novel cancer therapies, all spindle-targeted therapeutics in clinical use today act on only one protein, tubulin. Surprisingly, kinesin Eg5 expression is most abundant in proliferating human tissues, whereas it is absent from most postmitotic cells, such as e.g. human central nervous system neurons, consistent with an exclusive or almost confined role for Eg5 in cell proliferation. In contrary to drugs that directly interfere with microtubule dynamic instability, Eg5 kinesin inhibitors are expected not to disrupt microtubule-based cellular processes, e.g. neuronal vesicle transport, that are unrelated to proliferation. During mitosis, Eg5 is essentially involved in organizing microtubules into a bipolar structure that forms the mitotic spindle. Experimental perturbation of Eg5 function causes a characteristic malformation or dysfunction of the mitotic spindle, frequently resulting in cell cycle arrest and cell death.

The compounds according to this invention can be used to modulate mitotic spindle formation, thus causing prolonged cell cycle arrest in mitosis, which is frequently followed by apoptosis. By "modulate" herein is meant altering mitotic spindle formation, including increasing and decreasing spindle formation. By "mitotic spindle formation" herein is meant organization of microtubules into bipolar structures by mitotic kinesins. By "dysfunction of the mitotic spindle" herein is meant mitotic arrest and monopolar spindle formation. "Malformation of the mitotic spindle" encompasses the splaying of mitotic spindle poles, or otherwise causing morphological perturbation of the mitotic spindle.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include benign hypoplasia like that of the prostate ("BPH") or colon epithelium. Most importantly these diseases include malignant neoplasia commonly described as cancer and characterized by tumor cells finally metastasizing into distinct organs or tissues. Malignant neoplasia includes solid and hematological tumors. Solid tumors are exemplified by tumors of the breast, bladder, bone, brain, central and peripheral nervous system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasia include inherited cancers exemplified by retinomblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Compounds according to the present invention can be commercially applicable for treatment, prevention or amelioration of the diseases of benign and malignant behavior as described before.

Neoplastic cell proliferation might effect normal cell behaviour and organ function. For example the formation of new blood vessels, a process described as neovascularization, is induced by tumors or tumor metastases. Compounds according to this invention can be commercially applicable for the treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of compounds according to this invention is not limited to $1^{st}$ line treatment of patients. Patients with resistance to defined cancer chemotherapeutics or target specific anti-cancer drugs ($2^{nd}$ or $3^{rd}$ line treatment) can be also amenable for treatment with compounds according to this invention.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

Due to their cellular anti-proliferative properties, compounds according to the present invention may be also commercially usable for treatment of diseases associated with cell cycle and cell proliferation, such as, besides cancer discussed above, for example, fibroproliferative and differentiative disorders, psoriasis, rheumatoid arthritis, atherosclerosis, hyperplasia, restenosis, cardiac hypertrophy, (auto)immune disorders, fungal disorders, bone diseases, or acute or chronic inflammation.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a method useful to modulate apoptosis and/or aberrant cell growth in the therapy of benign or malignant neoplastic diseases, such as e.g. cancer, comprising administering to a subject in need of such therapy a pharmacologically active and therapeutically effective and tolerable amount of one or more of the compounds according to this invention.

The invention further includes a method for inhibiting Eg5 activity in cells comprising administering a pharmacologically active and therapeutically effective and tolerable amount of one or more of the compounds according to this invention to a patient in need of such inhibition.

The present invention further includes a method to modulate the mitotic spindle, i.e., for example, altering mitotic spindle formation, including decreasing spindle formation, or increasing or decreasing spindle pole separation causing malformation of the mitotic spindle poles, comprising administering a pharmacologically active and therapeutically effective and tolerable amount of one or more of the compounds according to this invention to a patient in need of such modulation.

The present invention further includes a method to inhibit mitosis in cells comprising administering a pharmacologically active and therapeutically effective and tolerable amount of one or more of the compounds according to this invention to a patient in need of such inhibition.

The present invention further relates to the use of the compounds according to this invention for the production of pharmaceutical compositions which are employed for the treatment, prophylaxis, inhibition and/or amelioration of the illnesses mentioned.

The present invention further relates to the use of the compounds according to this invention for the production of pharmaceutical compositions which can be used in the treatment, prevention or amelioration of hyperproliferative diseases of benign or malignant behaviour and/or disorders responsive to the induction of apoptosis in a mammal, such as e.g. cancer.

The present invention further relates to the use of the compounds according to this invention for the production of pharmaceutical compositions which can be used use in the treatment, prevention or amelioration of disorders responsive to arresting of aberrant cell growth and/or induction of apoptosis.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to combinations comprising one or more of the compounds according to this invention and pharmaceutically acceptable auxiliaries, excipients or vehicles, e.g. for use in the treatment, prevention or amelioration of benign or malignant neoplasia, such as e.g. cancer.

The present invention further relates to a composition consisting essentially of a therapeutically effective and tolerable amount of one or more compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration of hyperproliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to compounds according to this invention having Eg5 inhibiting properties.

The present invention further relates to pharmaceutical compositions according to this invention having Eg5 inhibiting properties.

The invention further relates to the use of a pharmaceutical composition comprising one or more of the compounds according to this invention as sole active Ingredient(s) and a pharmaceutically acceptable carrier or diluent in the manufacture of pharmaceutical products for the treatment and/or prophylaxis of the illnesses mentioned above.

The pharmaceutical compositions according to this invention can be prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before.

In one particular embodiment, compounds according to this invention may be combined with one or more art-known anti-cancer agents, such as e.g. with one or more chemotherapeutic and/or target specific anti-cancer agents as described below.

Examples of known chemotherapeutic anti-cancer agents frequently used for combination therapy include, but not are limited to (i) alkylating/carbamylating agents such as Cyclophosphamid (Endoxan®), Ifosfamid (Holoxan®), Thiotepa (Thiothepa Lederle®), Melphalan (Alkeran®), or chloroethylnitrosourea (BCNU); (ii) platinum derivatives like cis-platin (Platinex® BMS), oxaliplatin or carboplatin (Cabroplat® BMS); (iii) antimitotic agents/tubulin inhibitors such as vinca alkaloids (vincristine, vinblastine, vinorelbine, vinflunine), taxanes such as Taxol (Paclitaxel®), Taxotere (Docetaxel®) and analogs as well as new formulations and conjugates thereof, epothilones such as Epothilone B (Patupilone®), Azaepothilone (Ixabepilone®) or ZK-EPO, a fully synthetic epothilone B analog; (iv) topoisomerase inhibitors such as anthracyclines such as Doxorubicin (Adriblastin®), epipodophyllotoxines (such as Etoposide (Etopophos®) and camptothecin analogs such as Topotecan (Hycamtin®); (v) pyrimidine antagonists such as 5-fluorouracil (5-FU), Capecitabine (Xeloda®), Arabinosylcytosine/ Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pemetrexed (Alimta®).

Examples of target specific anti-cancer drug classes used in experimental or standard cancer therapy include but are not limited to (i) kinase inhibitors such as e.g. Glivec (Imatinib®), ZD-1839/Iressa (Gefitinib®), BAY43-9006 (Sorafenib®), SU11248 (Sutent®) or OSI-774/Tarceva (Erlotinib®); (ii) proteasome inhibitors such as PS-341 (Velcade®); (iii) histone deacetylase inhibitors like SAHA, PXD101, MS275, MGCD0103, CI-994, Depsipeptide/ FK228, NVP-LBH589, LAQ-824, Valproic acid (VPA) and butyrates; (iv) heat shock protein 90 inhibitors like 17-allylaminogeldanamycin (17-AAG); (v) vascular targeting agents (VATS) like combretastatin A4 phosphate or AVE8062/AC7700 and anti-angiogenic drugs like the VEGF antibody Avastin (Bevacizumab®) or the KDR tyrosine kinase inhibitor PTK787/ZK222584 (Vatalanib®); (vi) monoclonal antibodies such as Herceptin (Trastuzumab®), MabThera/Rituxan (Rituximab®) or C225/Erbitux (Cetuximab®) or Avastin (see above) as well as mutants and conjugates of monoclonal antibodies and antibody fragments; (vii) oligonucleotide based therapeutics like G-3139/Genasense (Oblimersen®); (viii) Toll-like receptor/TLR 9 agonists like Promune®; (ix) protease inhibitors (x) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known target specific anti-cancer agents which can be used for combination therapy include Neomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon α2 or interferon-γ, TRAIL, DR4/5 agonistic antibodies, FasL and TNF-R agonists.

As exemplary anti-cancer agents which can be useful in the combination therapy according to the present invention the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEXXAR, BICALUTAMIDE, BLEOMYCIN, BROXURIDINE, BUSULFAN, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEG-FILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE,.TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE, VOROZOLE and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents, such as e.g. those mentioned above (e.g. chemotherapeutic and/or target specific anti-cancer agents).

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous or chronologically staggered use in therapy, such as e.g. in therapy of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat hyperproliferative diseases and/or disorders responsive to the induction of apoptosis, such as e.g. cancer.

The present invention further relates to a combined preparation comprising at least one compound according to this invention and at least one art-known anti-cancer agent for simultaneous, sequential or separate administration.

In this connection, the present invention further relates to combinations, compositions, formulations, preparations or kits according to the present invention having anti-proliferative and/or apoptosis inducing properties.

Also in this connection, the present invention further relates to combinations, compositions, formulations, preparations or kits according to the present invention having Eg5 inhibitory activity.

In addition, the present invention further relates to a method for treating (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, particularly any of those cancer diseases mentioned herein, in a patient comprising administering a combination according to the present invention.

In addition, the present invention further relates to the use of a composition, combination, formulation, preparation or kit in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein.

The present invention further relates to the use of one or more of the compounds according to this invention for the manufacture of a medicament for use in combination with one or more anti-cancer agents, e.g. one or more anti-cancer agents selected from chemotherapeutic and target-specific anti-cancer agents, such as e.g. from those mentioned herein, for the treatment of cancer, particularly for the treatment of one of those cancer diseases mentioned above.

The present invention further relates to a commercial package comprising one or more compounds of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative disease and/or disorders responsive to induction of apoptosis, such as e.g. benign or malignant neoplasia, particularly one of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention can be in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention can be prepared by processes known per se. The dosage of the active compounds is carried out in the order of magnitude customary for Eg5 inhibitors, inhibitors for cellular proliferation or apoptosis inducers. Topical application forms (such as ointments) for the treatment of dermatoses thus contain the active compounds in a concentration of, for example, 0.1-99%. The customary dose in the case of systemic therapy (p.o.) is between 0.03 and 30 mg/kg per day, (i. v.) is between 0.03 and 30 mg/kg/h. In another embodiment, the dose in the case of systemic therapy (p.o.) is between 0.3 and 30 mg/kg per day, (i. v.) is between 0.3 and 30 mg/kg/h.

Biological Investigations

The ATPase activity of Eg5 kinesin motor domains (Cytoskeleton, cat. No. EG01) can be used to monitor the effects of modulating agents. The test compounds are dissolved as 10 mM solutions in dimethylsulfoxide (DMSO). 1 µl of appropriate DMSO dilutions of the test compounds are added to each well of a 96 well flat bottom plate. Each compound dilution is tested as duplicates. The reagents are added and the final reaction of the standard assay contains 15 mM Pipes, pH 6,8, 5.0 mM $MgCl_2$, 0.5 mM KCl, 1 mM EGTA, 0.1 mg/ml BSA, 0.025% Tween 20, 2 mM Glutathion, 5 µM Paclitaxel, 200 nM preformed microtubules (Cytoskeleton, cat. No. MT001), 300 µM ATP, and Eg5 protein (50 ng) in a reaction volume of 100 µl. The controls include buffer wells with ATP and 1% DMSO. Reactions are started by the addition of ATP, incubated at room temperature for 30 min., and terminated by removing 20 µl of the reaction volume and adding it to 80 µl of 1 M perchloric acid, followed by the addition of 80 µl Malachite green reagent. Malachite green reagent is prepared by mixing a solution of 4.2 g ammonium molybdate in 100 ml 4 N HCl with a solution of 0.135 g Malachite green in 300 ml $H_2O$. The reactions are incubated for a further 20 min. and then read at 615 nm.

The corresponding $IC_{50}$ values of the compounds for Eg5 inhibition are determined from the concentration-effect curves.

Representative inhibitory values [measured as $-\log IC_{50}$ (mol/l)] determined in the aforementioned assay follow from the following table A, in which the numbers of the compounds correspond to the numbers of the examples.

TABLE A

| Inhibition of Eg5 activity | |
|---|---|
| Compound | $-\log IC_{50}$ [mol/l] |
| 1, 2, 3, 4 and 5 | The inhibitory values of these listed compounds are all $\geq 6.9$ |

The anti-proliferative/cytotoxic activity of the compounds described herein can be tested on subclones of RKO human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 10 mM solutions in DMSO and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 µl per well. 24 hours after seeding the 50 µl each of the compound dilutions in DMEM medium are added into each well of the 96 well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The corresponding $IC_{50}$ values of the compounds for antiproliferative/cytotoxic activity are determined from the concentration-effect curves.

To determine the cell cycle specific mode of action, subclones of RKO colon adenocarcinoma cells (RKOp27 as described by Schmidt et al. in Oncogene 19, 2423-2429; 2000) are seeded into 96 well flat bottom plates at a density of 16000 cells per well in a volume of 50 µl per well in DMEM growth medium with 10% FCS containing 10 µM Ponasterone A. 24 hours after seeding the 50 µl each of the compound dilutions in DMEM medium are added into each well of the 96-well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Kip1 induced by Ponasterone A.

Representative values for anti-proliferation/cytotoxicity [measured as $-\log IC_{50}$ (mol/l)] determined in the aforementioned assays follow from the following table B, in which the numbers of the compounds correspond to the numbers of the examples.

TABLE B

Anti-proliferative/cytotoxic activity

| Compound | $-\log IC_{50}$ [mol/l] RKO p27 uninduced | $-\log IC_{50}$ [mol/l] RKO p27 induced |
|---|---|---|
| 1 | The $-\log IC_{50}$ values of these listed compounds are all $\geq 6.2$ | The $-\log IC_{50}$ values of these listed compounds are all $\leq 4$ |
| 2 | | |
| 3 | | |

The induction of apoptosis can be measured by using a Cell death detection ELISA (Roche Biochemicals, Mannheim, Germany). RKOp27 colon cancer cells are seeded into 96 well flat bottom plates at a density of 10000 cells per well in a volume of 50 µl RPMI medium (containing 10% fetal calf serum) per well. 24 hours after seeding the 50 µl each of the compound dilutions in RPMI medium are added into each well of the 96 Well plate. Each compound dilution is tested at least as triplicates. Wells containing untreated control cells are filled with 50 µl RPMI medium containing 1% DMSO. The cells are then incubated with the substances for 24 hours at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells are lysed in 200 µl lysis buffer. After centrifugation as described by the manufacturer, 10 µl of cell lysate is processed as described in the protocol. The degree of apoptosis is calculated as follows: The absorbance at 405 nm obtained with lysates from cells treated with 50 µM cisplatin is set as 100 cpu (cisplatin units), while an absorbance at 405 nm of 0.0 was set as 0.0 cpu. The degree of apoptosis is expressed as cpu in relation to the value of 100 cpu reached with the lysates obtained from cells treated with 50 µM cisplatin. The corresponding $EC_{50}$ values of the compounds for apoptosis inducing activity are determined from the concentration-effect curves.

Representative values for induction of apoptosis [measured as $-\log EC_{50}$ (mol/l)] determined in the aforementioned assays follow from the following table C, in which the numbers of the compounds correspond to the numbers of the examples.

TABLE C

Apoptosis Induction

| Compound | $-\log EC_{50}$ [mol/l] |
|---|---|
| 1, 2, 3 and 5 | The $-\log EC_{50}$ values of these listed compounds are all $\geq 5.6$ |

Experimental perturbation of Eg5 function causes a characteristic malformation of the mitotic spindle, which can be examined by confocal laser scanning microscopy. NCl-H460 non-small cell lung cancer cells are grown overnight on glass cover slips (Nunc™ Lab-Tek™ Chamber Slides) in 1800 µl DMEM medium containing 10% fetal calf serum. The test compounds are dissolved as 10 mM solutions in DMSO. Appropriate DMSO dilutions of the test compounds are further diluted 1:10 into DMEM medium containing 10% fetal calf serum to a final concentration ten times as much as the final concentration in the test. 24 hours after seeding, 200 µl of the compound dilutions in DMEM medium are added into each well of the cover slip. As a control, 200 µl DMEM medium containing 10% DMSO are added. 24 hours after incubation with the test compounds, the cells are washed with PBS, and fixed with 3.7% formaldehyde in $H_2O$ for 20 min. at 37° C. Subsequently, cells are washed with PBS and incubated with 0.1% Triton X-100 in a buffer containing 1.471 mM $KH_2PO_4$, 8.504 mM $Na_2HPO_4$, 137 mM NaCl, 1.325 mM $CaCl_2$, 2.685 mM KCl, 0.542 mM $MgCl_2$, pH 7.2 for 15 min. at room temperature. For saturation of non-specific binding, cells are incubated in 2% BSA/10% FCS in PBS (=blocking buffer) for 30 min. at room temperature prior to incubation with anti-alpha tubulin monoclonal antibodies (Sigma, #T5168; 1:1000), followed by Cy3-conjugated rabbit anti-mouse IgG (H+L) antibody (Jackson Immuno Research; 1:1000). All antibody incubations are performed for one hour at 37° C. in blocking buffer, and cells are washed three times in PBS between different incubations. DNA is counterstained with Hoechst 33342 (0.1 µg/ml). Coverslips are mounted in Vectashield (Vector Laboratories, Burlingame, Calif.) and examined with a Leica TCS SP2 confocal laser scanning microscope fitted with appropriate filters (Leica Microsystems, Bensheim, Germany). Representatively, the compounds numbered as Example 1 and Example 3 in this invention are tested in the aforementioned assay (application of each 1 µM) and are found to produce a significant enrichment of cells arrested in mitosis with rosettes of condensed mitotic chromosomes attached to radial arrays of microtubules.

The invention claimed is:

1. A combination comprising
a first active ingredient, which is at least one compound of formula (I*)

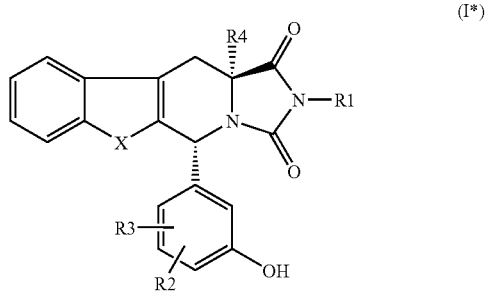

in which
R1 is 1-4C-alkyl, 3-7C-cycloalkyl, 3-7C-cycloalkyl-1-4C-alkyl, or 2-7C-alkyl substituted by R11,
R11 is —N(R111)R112,
R111 is hydrogen, or 1-4C-alkyl,
R112 is hydrogen, or 1-4C-alkyl,
or R111 and R112 together, and with inclusion of the nitrogen atom to which they are bonded, form a ring Het,
Het is piperidinyl, morpholinyl, thiomorpholinyl, or pyrrolidinyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy, and
X is NH, oxygen or sulphur, and
R4 is 1-4C-alkyl,
or
X is sulphur, and
R4 is hydrogen,
or
X is oxygen, and
R4 is hydrogen,
or
  (±)-(3aSR,10RS)-10-(3-Hydroxy-phenyl)-2,3a-dimethyl-3a,4,9,10-tetrahydro-2,9,10a-triaza -cyclopenty[b]fluorene-1,3-dione;
  (3aSR,10RS)-10-(3-Hydroxy-phenyl)-2,3a-dimethyl-4,10-dihydro-3aH-9-thia-2,10a-diaza -cyclopenta[b]fluorene-1,3-dione;
  (3aSR,10RS)-2-(2-Dimethylamino-ethyl)-10-(3-hydroxy-phenyl)-3a-methyl-3a,4,9,10-tetrahydro -2,9,10a-triaza-cyclopenty[b]fluorene-1,3-dione; or
  (3aSR,10RS)-2-(2-Dimethylamino-ethyl)-10-(3-hydroxy-phenyl)-3a-methyl-4,10-dihydro-3aH-9-thia-2,10a-diaza-cyclopenta[b]fluorene-1,3-dione
  or a salt, stereoisomer or a salt of a stereoisomer thereof; and
    a second active ingredient, which is at least one anti-cancer agent selected from the group consisting of chemotherapeutic anti-cancer agents and target-specific anti-cancer agents.

2. The combination according to claim 1, in which said chemotherapeutic anti-cancer agents are selected from the group consisting of (i) alkylating/carbamylating agents; (ii) platinum derivatives; (iii) antimitotic agents/tubulin inhibitors; (iv) topoisomerase inhibitors; (v) pyrimidine antagonists; (vi) purin antagonists and (vii) folic acid antagonists.

3. The combination according to claim 1, in which said target-specific anti-cancer agents are selected from the group consisting of (i) kinase inhibitors; (ii) proteasome inhibitors; (iii) histone deacetylase inhibitors; (iv) heat shock protein 90 inhibitors; (v) vascular targeting agents(VATS) and anti-angiogenic drugs; (vi) monoclonal antibodies as well as mutants and conjugates of monoclonal antibodies and antibody fragments; (vii) oligonucleotide based therapeutics; (viii) Toll-like receptor/TLR 9 agonists; (ix) protease inhibitors; and (x) hormonal therapeutics; bleomycin; retinoids; DNA methyltransferase inhibitors; alanosine; cytokines; interferons; TRAIL; DR4/5 agonistic antibodies; FasL and TNF-R agonists.

4. The combination according to claim 1, wherein in the compound of formula (I*)
  A)
  R1 is 1-2C-alkyl, cyclopropyl, cyclopropylmethyl, or 2-4C-alkyl substituted by R11,
R11 is —N(R111)R112,
R111 is 1-2C-alkyl,
R112 is 1-2C-alkyl,
or R111 and R112 together, and with inclusion of the nitrogen atom to which they are bonded, form a ring Het,
Het is piperidinyl, morpholinyl, thiomorpholinyl, or pyrrolidinyl,
R2 is hydrogen,
R3 is hydrogen, and
X is NH, oxygen or sulphur, and
R4 is methyl,
or
X is sulphur, and
R4 is hydrogen,
or
X is oxygen, and
R4 is hydrogen,
or
  B)
  R1 is 1-4C-alkyl, 3-7C-cycloalkyl, 3-7C-cycloalkyl-1-4C-alkyl, or 2-7C-alkyl substituted by R11,
R11 is —N(R111)R112,
R111 is hydrogen, or 1-4C-alkyl,
R112 is hydrogen, or 1-4C-alkyl,
or R111 and R112 together, and with inclusion of the nitrogen atom to which they are bonded, form a ring Het,
Het is piperidinyl, morpholinyl, thiomorpholinyl, or pyrrolidinyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy,
X is NH, oxygen or sulphur, and
R4 is 1-4C-alkyl,
or
  C)
  R1 is 1-4C-alkyl, 3-7C-cycloalkyl, 3-7C-cycloalkyl-1-4C-alkyl, or 2-7C-alkyl substituted by R11,
R11 is —N(R111)R112,
R111 is hydrogen, or 1-4C-alkyl,
R112 is hydrogen, or 1-4C-alkyl,
or R111 and R112 together, and with inclusion of the nitrogen atom to which they are bonded, form a ring Het,
Het is piperidinyl, morpholinyl, thiomorpholinyl, or pyrrolidinyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy,
X is sulphur, and
R4 is hydrogen,
or
  D)
  R1 is methyl, ethyl, or cyclopropyl,
R2 is hydrogen,
R3 is hydrogen,
X is NH, oxygen or sulphur, and
R4 is methyl,
or
  E)
  R1 is methyl, ethyl, or cyclopropyl,
R2 is hydrogen,
R3 is hydrogen, X is sulphur, and
R4 is hydrogen,
or
F)
R1 is methyl, ethyl, or ethyl substituted by R11,
R11 is —N(R111)R112,
R111 is methyl,
R112 is methyl,
or R111 and R112 together, and with inclusion of the nitrogen atom to which they are bonded, form a ring Het,
Het is morpholinyl,
R2 is hydrogen,
R3 is hydrogen, and
X is NH, oxygen or sulphur, and
R4 is methyl,
or
X is sulphur, and
R4 is hydrogen,
or
X is oxygen, and
R4 is hydrogen,
or
G)
R1 is methyl, or ethyl substituted by R11,
R11 is —N(R111)R112,
R111 is methyl,
R112 is methyl,
R2 is hydrogen,
R3 is hydrogen, and
X is NH, and
R4 is methyl,
or
X is sulphur, and
R4 is methyl,
or
X is oxygen, and
R4 is methyl,
or
H)
R1 is methyl, or ethyl substituted by R11,
R11 is —N(R111)R112,
R111 is methyl,
R112 is methyl,
R2 is hydrogen,
R3 is hydrogen, and
X is sulphur, and
R4 is hydrogen,
or
X is oxygen, and
R4 is hydrogen,
or
I)
R1 is methyl,
R2 is hydrogen,
R3 is hydrogen, and
X is NH, and
R4 is methyl,
or
X is sulphur, and
R4 is methyl,
or
X is oxygen, and
R4 is methyl,
or
J)
R1 is methyl,
R2 is hydrogen, R3 is hydrogen, and
X is sulphur, and
R4 is hydrogen,
or
X is oxygen, and
R4 is hydrogen,
or a pharmaceutically acceptable salt thereof.

5. The combination according to claim 1, wherein in the compound of formula (I*)
R2 and R3 are both hydrogen, and R1, R4 and X have any one of the meanings 1.1 to 1.6 given in the following table:

|  | R1 | R4 | X |
|---|---|---|---|
| 1.1 | —CH$_3$ | —CH$_3$ | NH |
| 1.2 | —CH$_3$ | —CH$_3$ | S |
| 1.3 | —CH$_2$CH$_2$—N(CH$_3$)$_2$ | —CH$_3$ | NH |
| 1.4 | —CH$_2$CH$_2$—N(CH$_3$)$_2$ | —CH$_3$ | S |
| 1.5 | —CH$_3$ | H | S |
| 1.6 | —CH$_2$CH$_2$—N(CH$_3$)$_2$ | H | S | or a pharmaceutically acceptable salt thereof.

6. The combination according to claim 1, wherein in the compound of formula (I*) R4 is 2-4C-alkyl.

7. The combination according to claim 1, wherein in the compound of formula (I*) R1 is 3-7C-cycloalkyl.

8. The combination according to claim 1, wherein in the compound of formula (I*) R1 is 3-7C-cycloalkyl-1-4C-alkyl.

9. The combination according to claim 1, wherein in the compound of formula (I*) R1 is 2-7C-alkyl substituted by R11.

10. The combination according to claim 1, wherein the compound of formula (I*) is selected from the group consisting of
(3aS,10R)-10-(3-Hydroxy-phenyl)-2,3a-dimethyl-3a,4,9,10-tetrahydro-2,9,10a-triaza-cyclopenty[b]fluorene-1,3-dione;
(3aS,10R)-10-(3-Hydroxy-phenyl)-2-methyl-4,10-dihydro-3aH-9-thia-2,10-diaza-cyclopenta[b]fluorene-1,3-dione;
(3aS,10R)-2-Butyl-10-(3-hydroxy-phenyl)-4,10-dihydro-3aH-9-thia-2,10a-diaza-cyclopenta[b]fluorene-1,3-dione;
(3aS,10R)-10-(3-Hydroxy-phenyl)-2,3a-dimethyl-4,10-dihydro-3aH-9-thia-2,10a-diaza-cyclopenta[b]fluorene-1,3-dione;
(3aS,10R)-2-(2-Dimethylamino-ethyl)-10-(3-hydroxy-phenyl)-3a-methyl-3a,4,9,10-tetrahydro-2,9,10a-triaza-cyclopenty[b]fluorene-1,3-dione;
(3aS,10R)-2-(2-Dimethylamino-ethyl)-10-(3-hydroxy-phenyl)-4,10-dihydro-3aH-9-thia-2,10-diaza-cyclopenta[b]fluorene-1,3-dione; and
(3aS,10R)-2-(2-Dimethylamino-ethyl)-10-(3-hydroxy-phenyl)-3a-methyl-4,10-dihydro-3aH-9-thia-2,10a-diaza-cyclopenta[b]fluorene-1,3-dione.

11. The combination according to claim 1, wherein the compound of formula (I*) is selected from the group consisting of
(±)-(3aSR,10RS)-10-(3-Hydroxy-phenyl)-2,3a-dimethyl-3a,4,9,10-tetrahydro-2,9,10a-triaza-cyclopenty[b]fluorene-1,3-dione;
(3aSR,10RS)-10-(3-Hydroxy-phenyl)-2,3a-dimethyl-4,10-dihydro-3aH-9-thia-2,10a-diaza-cyclopenta[b]fluorene-1,3-dione;

(3aSR,10RS)-2-(2-Dimethylamino-ethyl)-10-(3-hydroxy-phenyl)-3a-methyl-3a,4,9,10-tetrahydro-2,9,10a-triaza-cyclopenty[b]fluorene-1,3-dione; and (3aSR,10RS)-2-(2-Dimethylamino-ethyl)-10-(3-hydroxy-phenyl)-3a-methyl-4,10-dihydro-3aH-9-thia-2,10a-diaza-cyclopenta[b]fluorene-1,3-dione.

12. The combination according to claim 1, wherein in the compound of formula (I*)

i)
R1 is 2-4C-alkyl substituted by R11,
R11 is —N(R111)R112,
R111 is 1-2C-alkyl,
R112 is 1-2C-alkyl,
R2 is hydrogen,
R3 is hydrogen,
X is NH,
R4 is methyl,
or
ii)
R1 is 2-7C-alkyl substituted by R11,
R11 is —N(R111)R112,
R111 is hydrogen, or 1-4C-alkyl,
R112 is hydrogen, or 1-4C-alkyl,
R2 is hydrogen, 1-4C-alkyl, halogen, trifluoromethyl, 1-4C-alkoxy, hydroxyl, 1-4C-alkoxy-2-4C-alkoxy, hydroxy-2-4C-alkoxy, 3-7C-cycloalkoxy, 3-7C-cycloalkyl-1-4C-alkoxy, or completely or predominantly fluorine-substituted 1-4C-alkoxy,
R3 is hydrogen, or 1-4C-alkoxy,
X is NH, and
R4 is 1-4C-alkyl,
or
iii)
R112 is hydrogen,
R2 is hydrogen, and
R3 is hydrogen,
or a pharmaceutically acceptable salt thereof.

13. The combination according to claim 1, wherein in the compound of formula (I*)

X is NH, and R4 is methyl, and/or
R2 and R3 are both hydrogen, and/or
R1 is 2-(N,N-dimethylamino)-ethyl.

14. The combination according to claim 1, wherein in the compound of formula (I*)

R1 is 2-4C-alkyl substituted by R11,
R11 is —N(R111)R112,
R111 is hydrogen, or 1-4C-alkyl,
R112 is hydrogen, or 1-4C-alkyl.

* * * * *